United States Patent [19]
Zahiri et al.

[11] Patent Number: 5,645,079
[45] Date of Patent: Jul. 8, 1997

[54] APPARATUS FOR MECHANICALLY HOLDING, MANEUVERING AND MAINTAINING A BODY PART OF A PATIENT DURING ORTHOPEDIC SURGERY

[76] Inventors: Hormoz Zahiri; Christopher A. Zahiri, both of 11718 Chenault St., Los Angeles, Calif. 90049; Norman C. Christensen; Kenneth N. Christensen, both of 10702 Spyglass Hill Rd., Whittier, Calif. 90601

[21] Appl. No.: 348,321

[22] Filed: Dec. 2, 1994

[51] Int. Cl.⁶ .................................................. A61F 5/37
[52] U.S. Cl. ............... 128/846; 128/882; 602/32
[58] Field of Search .................... 128/845, 846, 128/869, 882; 269/328; 606/87; 602/32–36

[56] References Cited

U.S. PATENT DOCUMENTS

| | | | |
|---|---|---|---|
| 5,007,912 | 4/1991 | Albrektsson | 128/882 |
| 5,025,802 | 6/1991 | Laico | 128/882 |
| 5,056,535 | 10/1991 | Bonnell | 128/882 |
| 5,063,918 | 11/1991 | Guhl . | |
| 5,112,340 | 5/1992 | Krenkel et al. . | |
| 5,219,204 | 6/1993 | Bathrick | 297/321 |
| 5,219,349 | 6/1993 | Krag et al. . | |
| 5,290,220 | 3/1994 | Guhl | 602/32 |

FOREIGN PATENT DOCUMENTS

| | | |
|---|---|---|
| 1149959 | 4/1985 | U.S.S.R. . |
| 1205903 | 1/1986 | U.S.S.R. . |
| 1512585 | 10/1989 | U.S.S.R. . |

*Primary Examiner*—Michael A. Brown
*Attorney, Agent, or Firm*—Thomas I. Rozsa; Tony D. Chen

[57] ABSTRACT

The present invention is a novel and unique orthopedic apparatus for holding, maneuvering and maintaining a body part of a patient during orthopedic surgery. The orthopedic apparatus provides for assisting the primary surgeon during orthopedic surgery by holding, maneuvering and maintaining a patient's leg, thereby eliminating any assistant surgeon in the surgery operation. The orthopedic apparatus is capable of independently accomplishing transverse sliding, up-and-down tilting, lateral swinging, longitudinal extension/retraction, and axial rotation so that the surgeon can properly positioned a patient's leg for the orthopedic operation. The orthopedic apparatus has self-locking gear mechanisms to hold the various sections of the orthopedic apparatus in position to thereby hold the patient's leg in the proper position throughout the surgical operation. The orthopedic apparatus can be mechanically, electrically or hydraulically driven to adjust the orthopedic apparatus, so that the surgeon can position the patient's leg with great accuracy during surgery.

28 Claims, 6 Drawing Sheets

FIG.10 ical equipment. More particularly, the present invention relates to the field of medical equipment used in surgical operations.

APPARATUS FOR MECHANICALLY HOLDING, MANEUVERING AND MAINTAINING A BODY PART OF A PATIENT DURING ORTHOPEDIC SURGERY

BACKGROUND OF THE INVENTION

1. Field of The Invention

The present invention relates to the field of medical equipment. More particularly, the present invention relates to the field of medical equipment used in surgical operations.

2. Description of The Prior Art

Various devices used for assisting a surgeon during a surgery are known in the prior art. However, there is no prior art mechanical equipment which can be used to hold, maneuver and maintain a patient's leg in a specific position. Currently, when a surgeon is performing orthopedic surgery, e.g. knee surgery, the patient's lower extremity is held, maneuvered and maintained in a specific position by an assistant surgeon. One of the disadvantages in using an assistant surgeon is that it is not cost effective and the insurers or the patient have to pay the assistant surgeon in assisting in the surgical operation, an amount equal to 25% of the surgeon's fee. Another disadvantage is that during surgery, an assistant surgeon may not be able to maintain the leg's position as steadily as required by the surgeon and repeated readjustment may become necessary. In addition, an assistant surgeon is normally a practicing surgeon who is too busy with his own medical practice schedule. It is quite often difficult to find an appropriate time slot in the surgeon's weekly schedule, to schedule a surgery with them.

The inventors objective is to eliminate the assistant surgeon during surgery and provide an apparatus which can be easily operated to achieve high accuracy in holding, maneuvering and maintaining a patient's body part during orthopedic surgery.

The following six (6) prior art patents were uncovered in the pertinent field of the present invention.

1. U.S. Pat. No. 5,063,918 issued to Guhl on Nov. 12, 1991 for "Multi-Mode Distraction System For Ankle Arthroscopy" (hereafter "the Guhl Patent").

2. U.S. Pat. No. 5,112,340 issued to Krenkel et al. on May 12, 1992 for "Fixation Device With Frame Members And Pins" (hereafter "the Krenkel Patent").

3. U.S. Pat. No. 5,219,349 issued to Krag et al. on Jun. 15, 1993 for "Spinal Fixation Reduction Frame" (hereafter "the Krag Patent").

4. Soviet Patent No. 1,149,959 for "Bone Fragment Repositioning And Fixation Device—Motion Screws Bear Rotating Plates And Brackets Joined By Links To The Rotating Plates" (hereafter "the '959 Soviet Patent").

5. Soviet Patent No. 1,205,903 for "Femur And Humerus Periarticular Fracture Treatment Apparatus—Ring And Support Surfaces Are Set Parallel And Coaxially" (hereafter "the '903 Soviet Patent").

6. Soviet Patent No. 1,512,585 for "Ankle Joint Working Apparatus—With Toothed Wheel With Diametral Pin Attachment Projections And Worm With Flywheel" (hereafter "the '585 Soviet Patent").

The Guhl Patent discloses a multi-mode distraction system for ankle arthroscopy. The system includes an appropriate means for supporting the patient in a generally supine position and for adjustably supporting the patient's leg posteriorly of the knee joint in a manner to maintain the leg in a flexed position between slightly flexed and acutely flexed (e.g. a conventional gynecological or urological leg holder). The system includes non-invasive distraction means which are attached by opposite ends to the foot of the patient and the patient support means to provide a selectively variable tensile force on the ankle joint which is sufficient to provide an initial level of ankle joint distraction. The system also includes skeletal distraction means which includes a proximal end adapted to be pinned to the lower tibia and a distal end adapted to be attached to the heel bone to provide a selectively variable tensile force on the ankle joint sufficient to provide a greater level of ankle joint distraction force than the non-invasive means. The system also permits progression to heavy bilateral skeletal distraction.

The Krenkel Patent discloses a fixation device with frame members and pins. It includes a frame with three feet which can be mounted on pins anchored in the skeleton. The pins, which serve to fix the frame are designed as Kirschner's wires with ball ends. The ball end makes it possible to mount the hollow ends of the feet of the frame in different directions. The Kirschner's wire design allows the pins to be screwed into the bones due to the boring end that is typical for such wires.

The Krag Patent discloses an internal spinal fixation reduction frame. The Krag's device is for producing realignment of vertebrae affected by various spinal disorders, including fractures and dislocation. It includes three assemblies: two T-handles; a lower-rod assembly; and an upper-rod assembly. The reduction frame is secured to shaft handles extending from the pedicle screws of a Vermont Spinal Fixator type implant. Shaft clamps secure to the two T-handles to the shaft handles. The lower-rod assembly joins to the opposite T-frames by lower-rod clamps. The upper-rod assembly is also provided on the T-handles to produce rotation of the T-handles by changing the distance between the upper ends of the T-handles. Finger grips are provided on the upper-rod assembly to allow the surgeon to easily use one hand to either apply or monitor the force acting along the upper-rod.

The '959 Soviet Patent discloses a bone fragment repositioning and fixation device. The '959 Soviet's device assures the elimination of angle displacements in the sagittal and horizontal planes. It includes a base and carriages linked to motion screws on which two yokes are mounted with the possibility of motion in the horizontal, frontal and sagittal planes.

The '903 Soviet Patent discloses a femur and humerus periarticular fracture treatment apparatus. The Soviet's device allows for three dimensional joint head repositioning. It includes a ring with guides, runners and a support surface with coaxial screws. The runners are linked to the coaxial screws. Projecting plates are arranged round the ring and hinged to it so that their angle of slant can be changed. The '903 Soviet Patent is an external device that can maneuver the segment of the head to position and alignment with the distal segment of the neck of the femur.

The '585 Soviet Patent discloses an ankle joint working apparatus. The Soviet's device eliminates adduction and rotation of the front part of the foot. It includes a toothed wheel having diametral projections for the attachment of pins and a worm with a flywheel which is mounted on a closing yoke of the foot. The '585 Soviet Patent sends pins through the bone and connects the ends of the pins together.

None of these prior art patents have disclosed an orthopedic apparatus which is designed and constructed for mechanically holding, maneuvering and maintaining a body part of a patient during an orthopedic surgery, so that a surgeon can perform the orthopedic surgery without an assistant surgeon. It is highly desirable to have a very efficient and also very effective design and construction of an orthopedic apparatus for mechanically holding, maneuvering and maintaining a body part of a patient during orthopedic surgery, thereby eliminating the assistant surgeon from the surgical operation. It is desirable to provide an apparatus with the capability of rapidly changing the angle of the patient's leg during surgery. It is also desirable to provide an apparatus that is flexible enough to allow repositioning of the limb and the joint during the surgical procedure to provide optimum access to all of the available surgical entrant locations in a much more efficient way.

SUMMARY OF THE INVENTION

The present invention is a novel and unique orthopedic apparatus for mechanically holding, maneuvering and maintaining a body part of a patient during orthopedic surgery. The primary objective of the present invention is to provide an orthopedic apparatus for assisting a primary surgeon in performing orthopedic surgery by holding, maneuvering and maintaining a patient's leg, thereby eliminating any assistant surgeon during the surgical operation. It is another objective of the present invention to provide a device which mechanically holds the lower extremity of a patient, and mechanically maneuvers the extremity into any intended position for the knee joint, and mechanically maintains that exact position as long as needed. These mechanical functions may be repeated frequently during a knee surgery procedure by the surgeon.

It is therefore an object of the present invention to provide an orthopedic apparatus which can be easily operated to achieve high accuracy in holding, maneuvering and maintaining a body part of a patient during orthopedic surgery, thereby eliminating the assistant surgeon during the surgical operation.

It is also object of the present invention to provide an orthopedic apparatus which is capable of independently accomplishing transverse sliding, up-and-down tilting, lateral swinging, longitudinal extension/retraction, and axial rotation, so that a surgeon can easily and properly position a patient's leg during orthopedic surgery.

It is an additional object of the present invention to provide an orthopedic apparatus which has self-locking gear mechanisms to hold the various sections of the orthopedic apparatus in position, and thereby hold and maintain the patient's leg in the proper position throughout the surgical operation.

It is a further object of the present invention to provide an orthopedic apparatus which can be manually adjusted, so that the surgeon can position the patient's leg with great flexibility during orthopedic surgery.

It is an additional object of the present invention to provide an orthopedic apparatus which can be electrically driven by motors to adjust the orthopedic apparatus, so that the surgeon can position the patient's leg with great easiness during orthopedic surgery.

It is a further object of the present invention to provide a computerized orthopedic apparatus which can be controlled by a computer or a joy-stick to adjust the orthopedic apparatus, so that the surgeon can position the patient's leg with great accuracy during orthopedic surgery.

Described briefly, the present invention is an orthopedic apparatus which includes a clamping section, a tilting section, a swinging section, and an extended rotatable section. The clamping section includes a cross bar, two clamping blocks attached to the opposite ends of the cross bar, and a sliding block slidably attached on the cross bar between the two clamping blocks. Two extension rods are fixed on and extend from the two clamping blocks respectively. The extension rods can be inserted into and secured by conventional clamps at the end of an operating table. Once the two extension rods are securely attached to the operating table, the cross bar is held by the two clamping blocks and positioned at close proximity to the end of the operating table, and the remaining sections of the orthopedic apparatus extend from the end, and along the longitudinal direction, of the operating table and generally parallel to the floor. The sliding block can be slid on the cross bar in a transverse direction.

The tilting section includes a gear box which is attached to the sliding block and a tilting part tiltably connected to the gear box. The gear box has a gear mechanism for adjusting the up-and-down tilting of the tilting part and the remaining sections of the orthopedic apparatus. A spring loaded lever is utilized for quick and rough tilt adjustment, and a pair of tilting wheels are utilized for fine-tuning the tilting of the tilting part. The tilting part can be tilted up-and-down by first releasing the lever and thereafter rotating the pair of tilting wheels.

The swinging section includes a gear box connected to the tilting part and a swinging part swingably connected to the gear box. The gear box has a gear mechanism and utilizes a pair of swinging wheels for adjusting the lateral swinging of the swinging section, and the remaining section of the orthopedic apparatus.

The extended rotatable section includes a gear box connected to the tilting part and an elongated sliding track rotatably connected to the gear box. The length of the sliding track can be adjusted to fit the length of the patient's leg. A disposable padding is provided for receiving the patient's ankle and foot. The gear box has a gear mechanism and utilizes a pair of rotation wheels to rotate the elongated sliding track about its longitudinal axis.

When a patient is lying on the operating table, the patient's buttocks are adjacent to the end of the operating table. The surgeon can slide the sliding block to align the apparatus with the patient's leg which is to be operated on. Then the surgeon can adjust the tilting, swinging, length and rotation of the respective sections of the apparatus to maneuver the patient's leg so it is properly positioned for the orthopedic operation. Once proper adjustment is achieved, the self-locking gear mechanisms of the apparatus hold the various sections of the apparatus in position, and thereby hold and maintain the patient's leg in the proper position throughout the surgical operation. If needed, the surgeon can mechanically adjust the position of the patient's leg from time to time with great accuracy.

The orthopedic apparatus can be adjusted in many ways including transverse sliding, up-and-down tilting, lateral swinging, longitudinal extension/retraction, and axial rotation.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Described briefly, the present invention is an orthopedic apparatus which includes a clamping section, a tilting section, a swinging section, and an extended rotatable section. The clamping section includes a cross bar, two clamping blocks attached to the opposite ends of the cross bar, and a sliding block slidably attached on the cross bar between the two clamping blocks. Two extension rods are fixed on and extend from the two clamping blocks respectively. The sliding block can be slid on the cross bar in a transverse direction.

The tilting section includes a gear box which is attached to the sliding block and a tilting part tiltably connected to the gear box. The gear box has a gear mechanism for adjusting the up-and-down tilting of the tilting part and the remaining sections of the orthopedic apparatus. A spring loaded lever is utilized for quick and rough tilt adjustment of the tilting part, and a pair of tilting wheels are utilized for fine tuning the tilting of the tilting part. The tilting part can be tilted up-and-down by first releasing the lever and thereafter rotating the pair of tilting wheels.

The swinging section includes a gear box connected to the tilting part and a swinging part swingably connected to the gear box. The gear box has a gear mechanism and utilizes a pair of swinging wheels for adjusting the lateral swinging of the swinging section, and the remaining section of the orthopedic apparatus.

The extended rotatable section includes a gear box connected to the tilting part and an elongated sliding track rotatably connected to the gear box. The length of the sliding track can be adjusted to fit the length of the patient's leg. A disposable padding is provided for receiving the patient's ankle and foot. The gear box has a gear mechanism and utilizes a pair of rotation wheels to rotate the elongated sliding track about its longitudinal axis.

The orthopedic apparatus mechanically holds the lower extremity of a patient, and mechanically maneuvers the lower extremity into any intended position for the knee joint, and mechanically maintains that exact position as long as needed. These mechanical functions may be repeated frequently during a knee surgery procedure by the surgeon.

Figure 1:
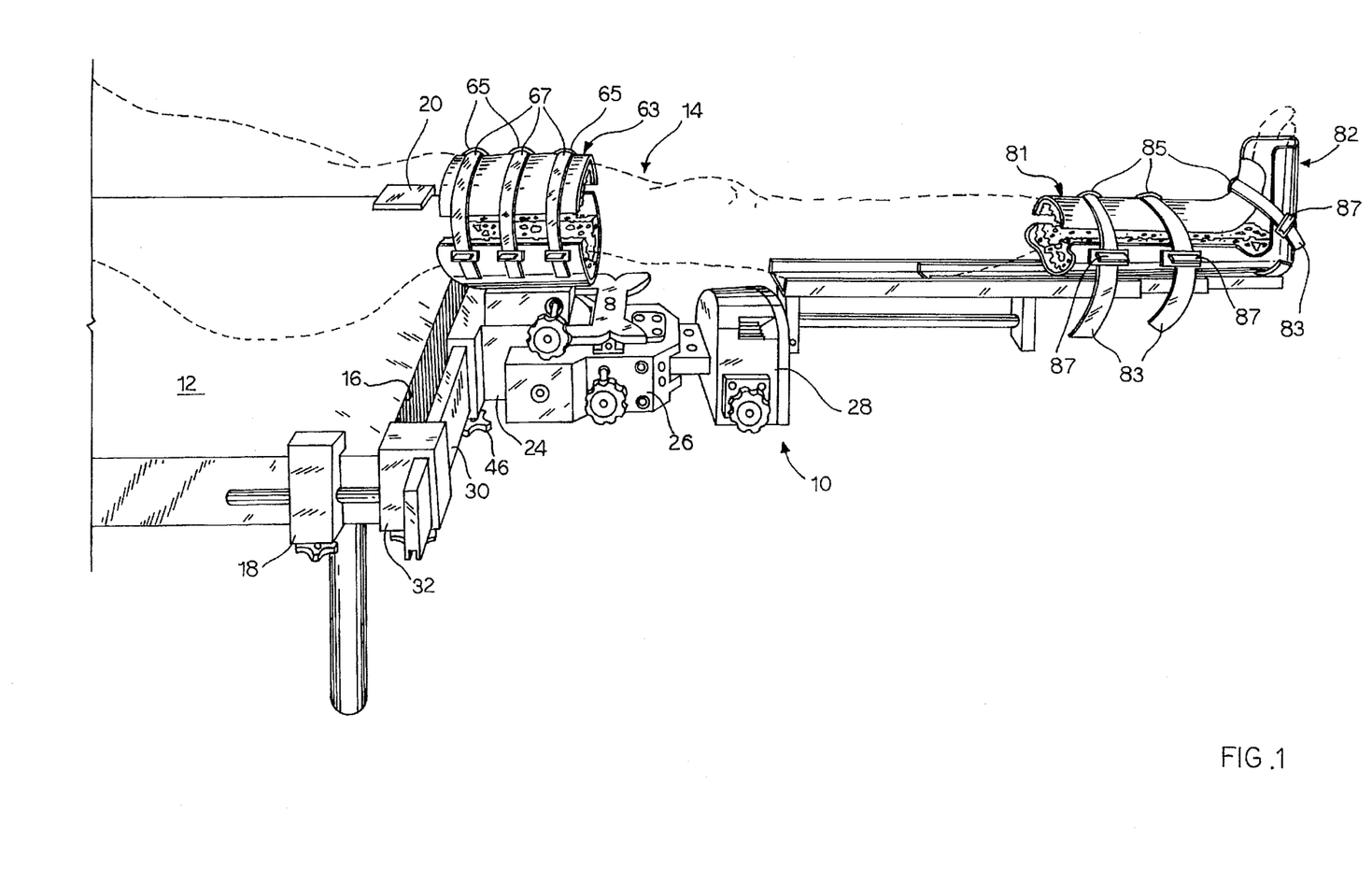
FIG. 1 is a perspective view of the preferred embodiment of the present invention orthopedic apparatus which is attached to the end of an operating table.
Figure 2:
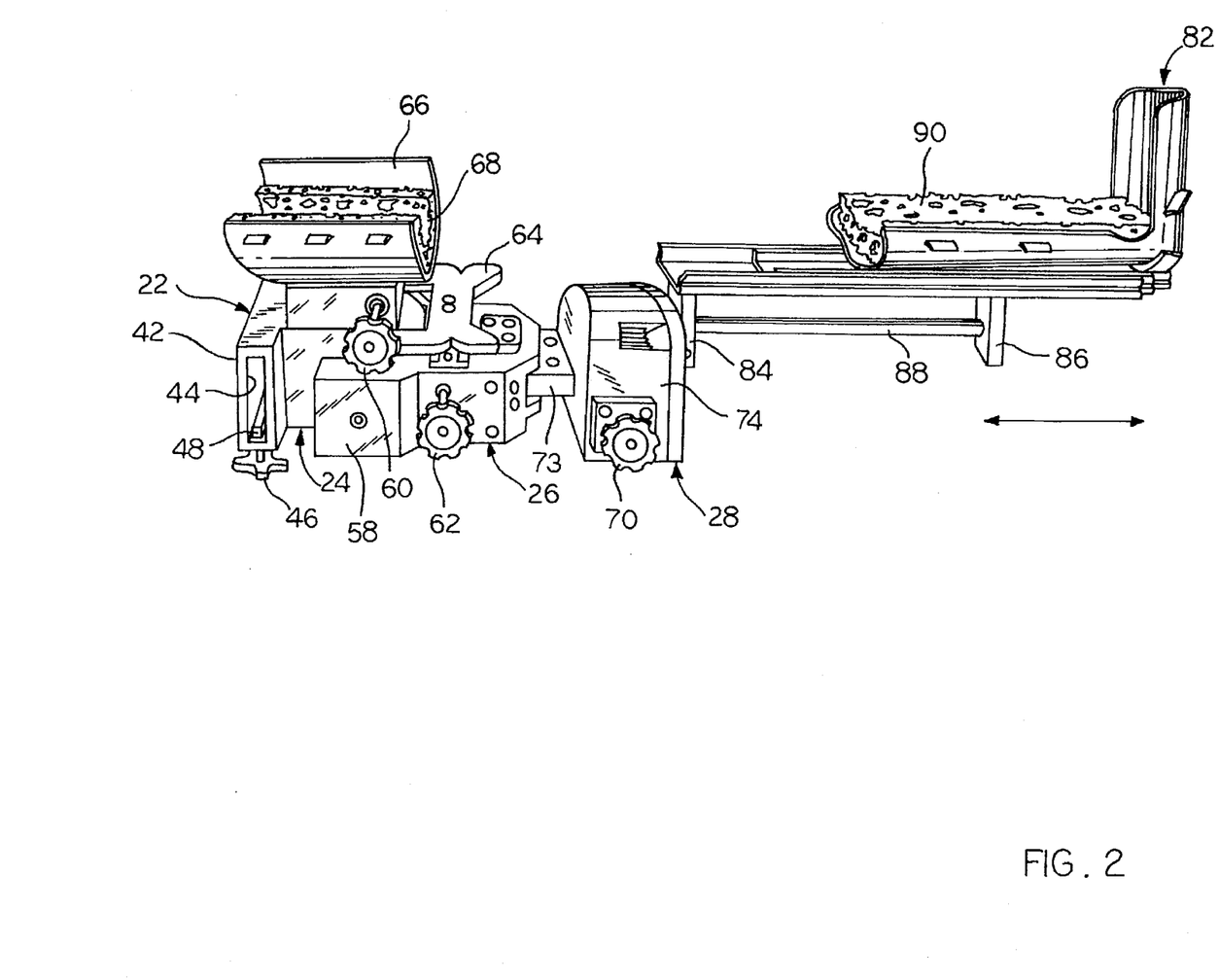
FIG. 2 is a perspective view of the present invention orthopedic apparatus which is extending in the longitudinal direction, where the longitudinal sliding track is fully retracted.

Referring to FIG. 1, there is shown at 10 the present invention orthopedic apparatus for mechanically holding, maneuvering and maintaining a body part of a patient 14, e.g. a knee during an orthopedic surgery. At present, when a surgeon is performing a knee surgery on the patient's leg, the patient's leg is held and maneuvered by an assistant surgeon. The orthopedic apparatus 10 eliminates the need for any assistant surgeon to hold, maneuver and maintain the patient's leg during orthopedic surgery.

The present invention orthopedic apparatus 10 includes five basic adjustments or movements: transverse sliding, up-and-down tilting, lateral swinging, longitudinal extension/retraction, and axial rotation. These five basic adjustments allow the orthopedic apparatus 10 to be very versatile during orthopedic surgery.

The orthopedic apparatus 10 is used in conjunction with an operating table 12 which has two opposite clamps 18 and 20 which are conventionally used in hospitals and medical clinics. The two opposite clamps 18 and 20 are located on the two opposite sides of the operating table 12 respectively. The orthopedic apparatus 10 is secured at the end 16 of the operating table 12 by the two opposite clamps 18 and 20 as shown. The patient 14 is illustrated in dashed lines and is lying on the operating table 12 with the leg strapped to the orthopedic apparatus 10.

It will be appreciated that the present invention orthopedic apparatus 10 can be affixed to a cabinet or cart with rollers and can be rolled up to the end 16 of the operating table 12 and secured therein, so that the apparatus 10 can easily be transportable.

Figures 5, 7:
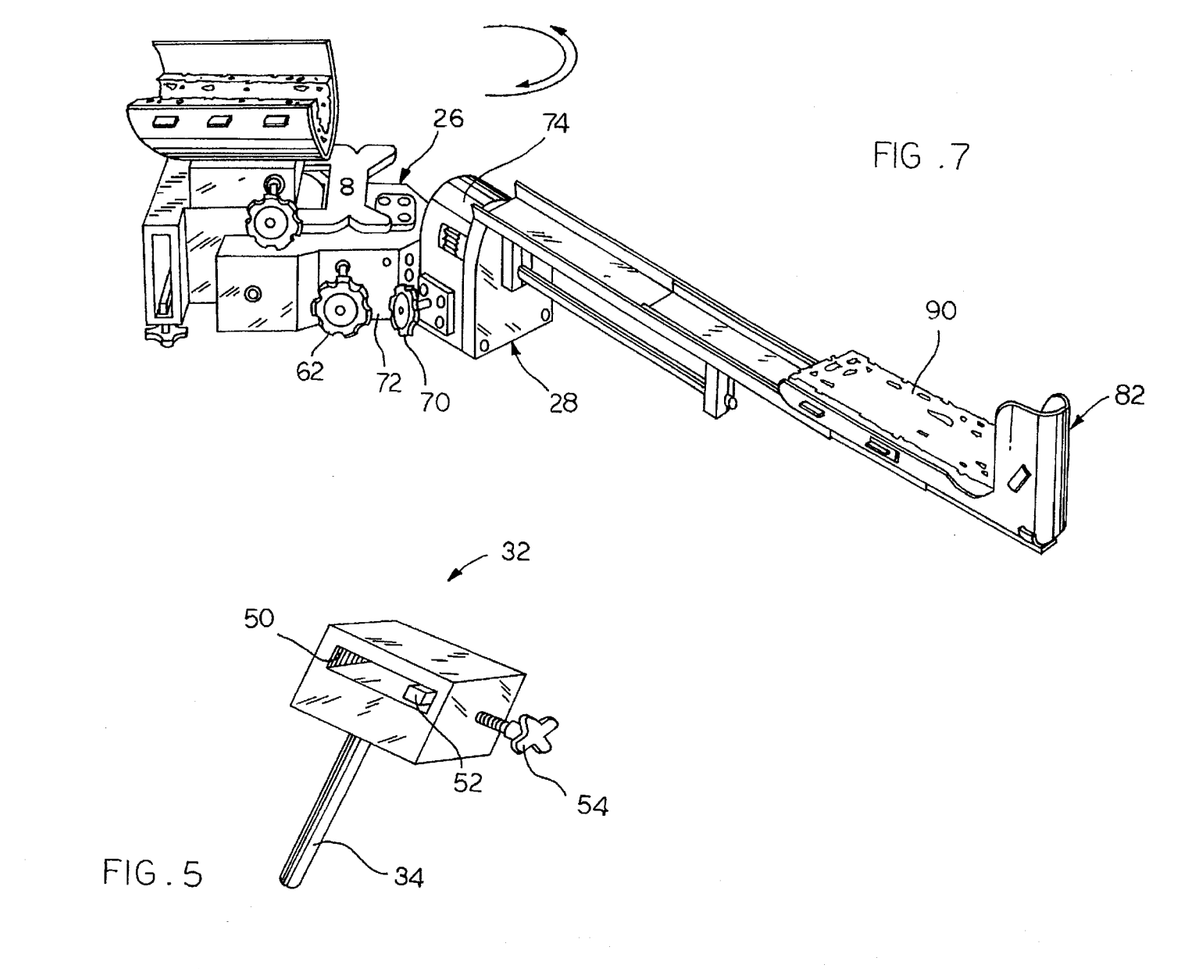
FIG. 5 is a perspective view of one of the two clamping blocks.
FIG. 7 is a perspective view of the present invention orthopedic apparatus illustrating one of its many swinging sections.

Referring to FIGS. 1 through 5, there is shown the orthopedic apparatus 10 which includes a clamping section 22, a tilting section 24, a swinging section 26, and an extended rotatable section 28. The orthopedic apparatus 10 also includes an elongated cross bar 30 (shown in detail in FIGS. 3 and 4), and two clamping blocks 32 (only one is shown in FIG. 5) attached to opposite ends 36 and 38 of the cross bar 30 respectively.

Figures 3, 4, 6:
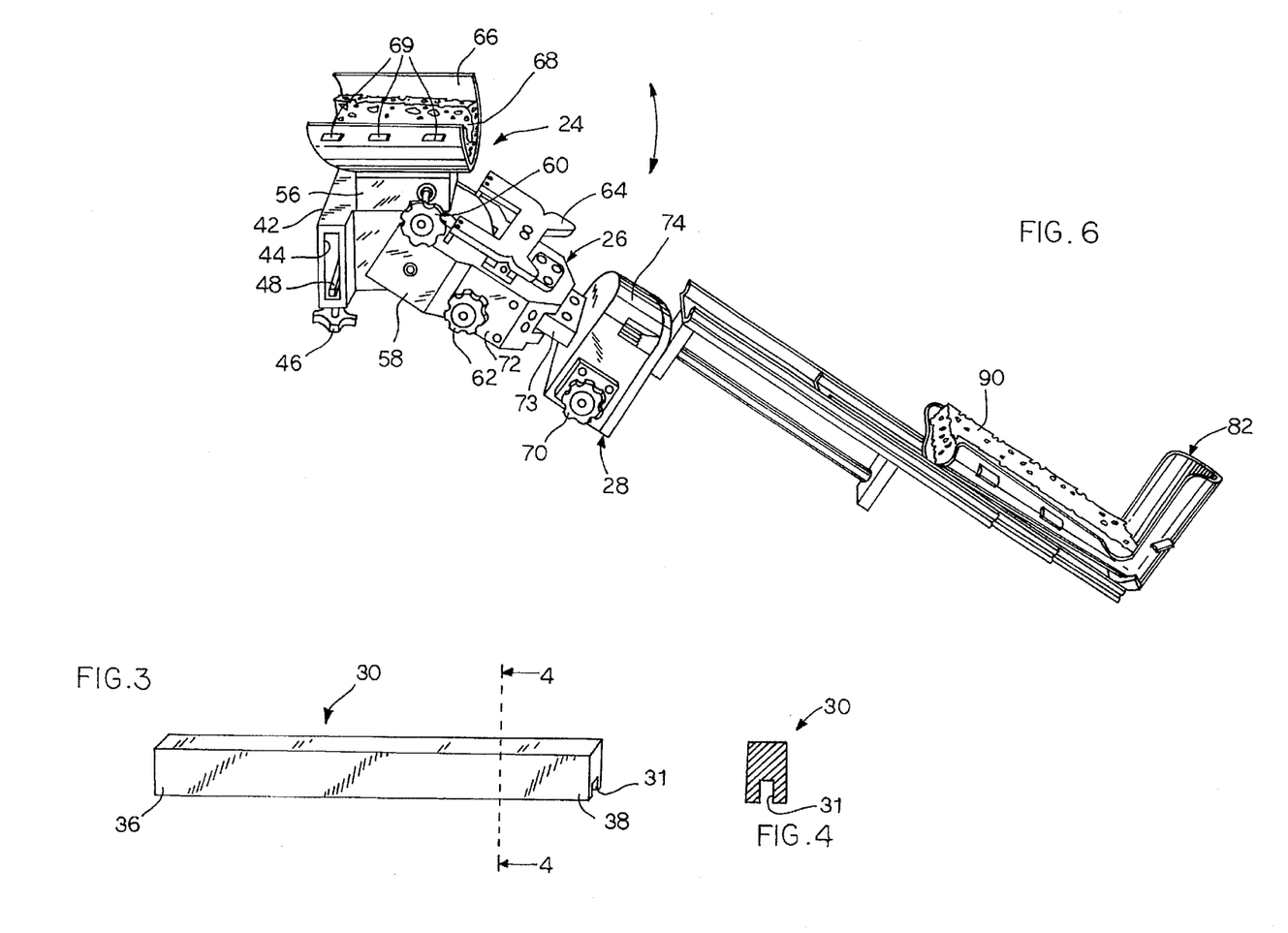
FIG. 3 is a perspective view of the elongated cross bar of the clamping section.
FIG. 4 is a cross-sectional view of the cross bar.
FIG. 6 is a perspective view of the present invention orthopedic apparatus illustrating one of its many tilting positions.

The clamping section 22 includes a sliding block 42 having a slotted opening 44 and slidably attached on the cross bar 30 between the two clamping blocks 32, as shown in FIG. 1. Two clamp fasteners 46 (only one is shown in FIG. 1) are located underneath the sliding block 42 for securing the cross bar 30 therein. Referring to FIGS. 3 and 4, the cross bar 30 has an elongated groove 31 extending from one end 36 to the other end 38 for engaging with a flange 48 which is located within the slotted opening 44 of the sliding block 42.

Referring to FIG. 5, there is shown one of the two clamping blocks 32. The two clamping blocks 32 are substantially identical, and to the extent they are, only one will be described in detail. An extension rod 34 is integrally formed on and extending from the clamping block 32. The clamping block 32 has a slotted opening 50 with a flange 52 mounted within the slotted opening 50 such that the flange 52 is perfectly sized to fit the groove 31 on the cross bar 30. Once the cross bar 30 is inserted into the slotted opening 50, a clamp handle 54 can be tighten to secure the clamping block 32 on the cross bar 30. The extension rods 50 of the clamping blocks 32 are inserted respectively into and secured by the two opposite clamps 18 and 20 at the end 16 of the operating table 12, as shown in FIG. 1. The cross bar 30 is positioned at close proximity to the end 16 of the operating table 12, and the remaining sections of the orthopedic apparatus 10 extend from the end 16, and along the longitudinal direction of the operating table 12, and generally parallel to the floor.

It will be appreciated that the clamping section 22 is not limited as shown in the figures. An attaching means section can be incorporated with the present invention orthopedic apparatus 10. It is emphasized that while the clamping section 22 as described is the preferred embodiment, it is also within the spirit and scope of the present invention to have many ways of attaching the orthopedic apparatus 10 to the operating table 12.

Referring to FIG. 6, there is shown the orthopedic apparatus 10 in one of its many tilting positions. The tilting section 24 includes a tilting gear box 56 or tilting means which is fixedly or integrally attached to the sliding block 42, and a tilting part 58 which is hingeably connected to the tilting gear box 56. The gear box 56 has a conventional self-locking worm gear mechanism (shown in detail in FIG. 9), and the description thereof will described later. The tilting wheels 60 are engagably connected to the gear mechanism of the gear box 56 for adjusting the up-and-down tilting of the tilting part 58 as well as the remaining sections of the orthopedic apparatus 10. The tilting wheels 60 are utilized for fine turning of the tilting part 58. A spring loaded lever 64 is mounted on top of the swinging gear box 72 of the swinging section 26. The spring loaded lever 64 is integrally connected to the gear mechanism of the tilting gear box 56 for providing a quick and rough adjustment of the tilting part 58 and the remaining sections of the orthopedic apparatus 10. The arrows in this figure illustrates the directions of the tilting part 58, the swinging section 26 and the extended rotatable section 28 are tilted.

Referring to FIGS. 1 and 6, a lower U-shaped thigh support holder 66 is hingeably attached to the top of the gear box 56 of the tilting section 24 for receiving the patient's thigh thereto. The U-shaped thigh support holder 66 has means for securing the patient's thigh to the thigh support holder 66, e.g. strap and buckle type fasteners 67 (as shown in FIG. 1 ). A disposable padding 68 is affixed to the thigh support holder 66 so that the patient's thigh is supported comfortably within the support holder 66 and is also used to keep the apparatus 10 sanitized. An upper inverted U-shaped thigh holder 63 is provided unattached, but is used for applying pressure on top of the person's thigh so the thigh will not move during the orthopedic surgery. The upper inverted U-shaped thigh holder 63 is provided with at least three loop eyelets or collars 65 for allowing the fasteners 67 to be inserted therethrough and secured to latches 69 on the U-shaped thigh support holder 66. The upper thigh holder 63 is secured on top of the person's thigh so that it is applying pressure thereto and is substantially parallel to the lower support holder 66. The upper thigh holder 63 is also provided with a disposable padding which is affixed thereto.

The orthopedic apparatus 10 can be manufactured with or without the thigh support holder 66. The orthopedic apparatus 10 can use any other means for supporting and securing the patient's thigh to the apparatus 10.

Referring to FIG. 7, there is shown the swinging of the orthopedic apparatus 10 in one of its many lateral positions. The swinging section 26 includes a swinging gear box 72 or swinging means and a swinging part 73 (which is visible in FIGS. 2 and 6). The swinging gear box 72 is integrally or fixedly attached to the tilting part 58 of the tilting section 24. The swinging part 73 is hingeably connected to the swinging gear box 72. The swinging gear box 72 has a self-looking worm gear mechanism (shown in detail in FIG. 9) which is similar to the gear mechanism of the tilting section 24. The pair of swinging wheels 62 are engagably connected to the gear mechanism of the gear box 72 for adjusting a lateral swinging of the swinging part 73 and the extended rotatable section 28 of the orthopedic apparatus 10. The arrows in this figure illustrates the swinging directions of the swinging part 73 and the extended rotatable section 28.

Figures 8, 9:
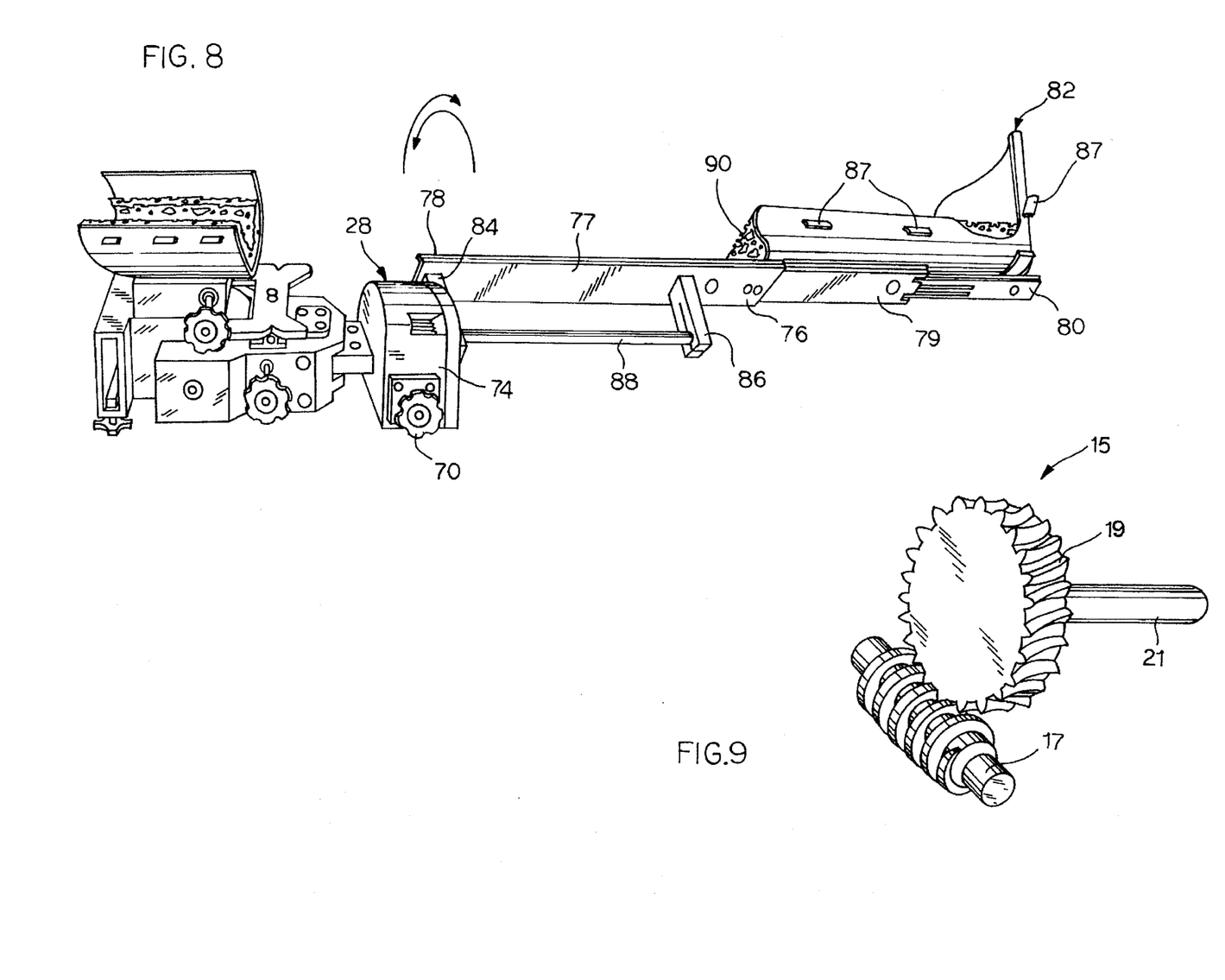
FIG. 8 is a perspective view of the present invention orthopedic apparatus illustrating one of the many rotational positions of the extended rotatable section.
FIG. 9 is a perspective view illustrating one of the self-locking gear mechanism utilized in the respective gear box of the tilting, swinging and extended rotatable sections.

Referring to FIG. 8, there is shown the extended rotatable section 28 of the orthopedic apparatus 10 in one of its many rotational positions. The extended rotatable section 28 includes a rotation gear box 74 or rotation means and an elongated sliding track 76. The rotation gear box 74 is integrally or fixedly attached to the swinging part 73 of the swinging section 26. The sliding track 76 is rotatably connected to the rotation gear box 74. The gear box 74 has a self-locking worm gear mechanism (shown in detail in FIG. 9) which is similar to the gear mechanisms of the tilting and swinging sections 24 and 26. The rotation wheels 70 are engagably connected to the gear mechanism of the gear box 74 for rotating the elongated sliding track 76 about its longitudinal axis.

The elongated sliding track 76 includes a proximal portion 77 and a distal portion 79 which slides within the proximal portion 77 so that the sliding track 76 can be extended or retracted. The sliding track 76 has one end 78 adjacent to the gear box 74 and the other end 80 having a foot holder 82 for receiving the patient's ankle and foot. The foot holder 82 has means for securing the ankle and foot to the foot holder, e.g. strap and buckle type fasteners 83 (as shown in FIG. 1).

Referring to FIGS. 1 and 8, an elongated L-shaped upper cover 81 is also provided with the foot holder 82. The upper cover 81 is unattached, but is used for applying pressure on the top portions of the patient's ankle and foot so the ankle and foot will not move during the orthopedic surgery. The upper cover 81 is provided with at least three loop eyelets or collars 85 for allowing the fasteners 83 to be inserted therethrough and secured to latches 87 on the foot holder 82. The upper cover 81 is secured on the top of the ankle so that it is applying pressure thereto and is substantially parallel to the foot holder 82. The upper cover 81 is also provided with a disposable padding which is affixed thereto.

The sliding track 76 is slidably adjustable to adjust the length of the sliding track 76 to fit the patient's leg and it automatically compensates for the patient's leg when the tilting section 24 is tilted. This sliding mechanism allows for changes in the length of the leg joint, and creates a slide compensation for the changes caused by the tilting of the tilting section 24.

Two support shafts 84 and 86 are attached at the bottom of the proximal portion 77 and spaced apart by an elongated rod 88. The elongated rod 88 is engagably connected to the gear mechanism of the rotation gear box 74 for rotating the sliding track 76. A disposable padding 90 is also provided within the foot holder 82. The arrows in this figure illustrate the directions that the extended rotatable section 28 may be rotated.

Referring to FIG. 9, there is shown the gear mechanism 15 for the tilting, swinging and the extended rotatable sections of the orthopedic apparatus 10. The gear mechanism 15 is conventional, and will only be described generally. The gear mechanism 15 includes a worm 17 and a worm wheel 19. The worm 17 is of helical shape, forming a continuous "tooth". The worm wheel 19 has independent teeth and is driven by the rotation of the worm 17 with which it meshes. The worm wheel 19 has a shaft 21 which is integrally connected to the respective tilting, swinging and the extended rotatable sections. The worm 17 has two ends which are connected to the respective wheels of the tilting, swinging and the extended rotatable sections.

An important aspect of the present invention apparatus 10 is the ability to hold and maintain the patient's leg in the proper position throughout the surgical operation. If needed, the surgeon can readjust the position of the patient's leg from time to time with great accuracy without an assistant surgeon. The pitch on the gear mechanisms will not allow it to move once the adjustments have been made by the surgeon. This will cause no backlash on the orthopedic apparatus 10.

Another important aspect of the present invention orthopedic apparatus 10 is the capability of independent adjustments in the transverse sliding, up-and-down tilting, lateral swinging, longitudinal extension/retraction, and axial rotation.

It will be appreciated that the orthopedic apparatus 10 is not limited to the worm gear mechanisms as described above. It is emphasized that while the worm gear mechanisms are the preferred embodiment, it is also within the spirit and scope of the present invention to have other type of gear mechanisms incorporated with the present invention orthopedic apparatus 10.

It will also be appreciated that the orthopedic apparatus 10 is not limited to mechanically adjusting the various sections of the orthopedic apparatus 10. It is emphasized that while the preferred embodiment of the orthopedic apparatus 10 is mechanically operated, it is also within the spirit and scope of the present invention to have the orthopedic apparatus 10 driven by electrical or hydraulic mechanisms or be computerized.

The orthopedic apparatus 10 can be made from several materials. The manufacturing process which could accommodate the construction of the orthopedic apparatus can be casting, injection, thermoform, etc. or other molding process. By way of example, the orthopedic apparatus 10 is preferably made of composite material or aluminum material or any other light-weight high strength material. The present invention orthopedic apparatus 10 conforms to conventional forms of manufacture and is easy to use so it provides a device that will be economically feasible, long lasting and relatively trouble-free in operation.

The operation of the foregoing embodiment will be described now. When a patient is lying on the operating table, the patient's buttocks are adjacent to the end of the operating table. The surgeon can slide the sliding block to align the apparatus with the patient's leg which is to be operated on. Then the surgeon can adjust the tilting, swinging, length and rotation of the respective sections of the orthopedic apparatus to maneuver the patient's leg so it is properly positioned for the orthopedic operation. Once proper adjustment is achieved, the self-locking gear mechanisms of the apparatus hold the various sections of the apparatus in position to thereby hold and maintain the patient's leg in the proper position throughout the surgical operation. If needed, the surgeon can adjust the position of the patient's leg from time to time with great accuracy.

The unique features of the orthopedic apparatus design include not only that it can be adjusted in the tilting, swinging, length and rotation of the respective sections independently but also that it allows a surgeon to accomplish those adjustments independently of one another without the need of an assistant surgeon.

Figure 10:
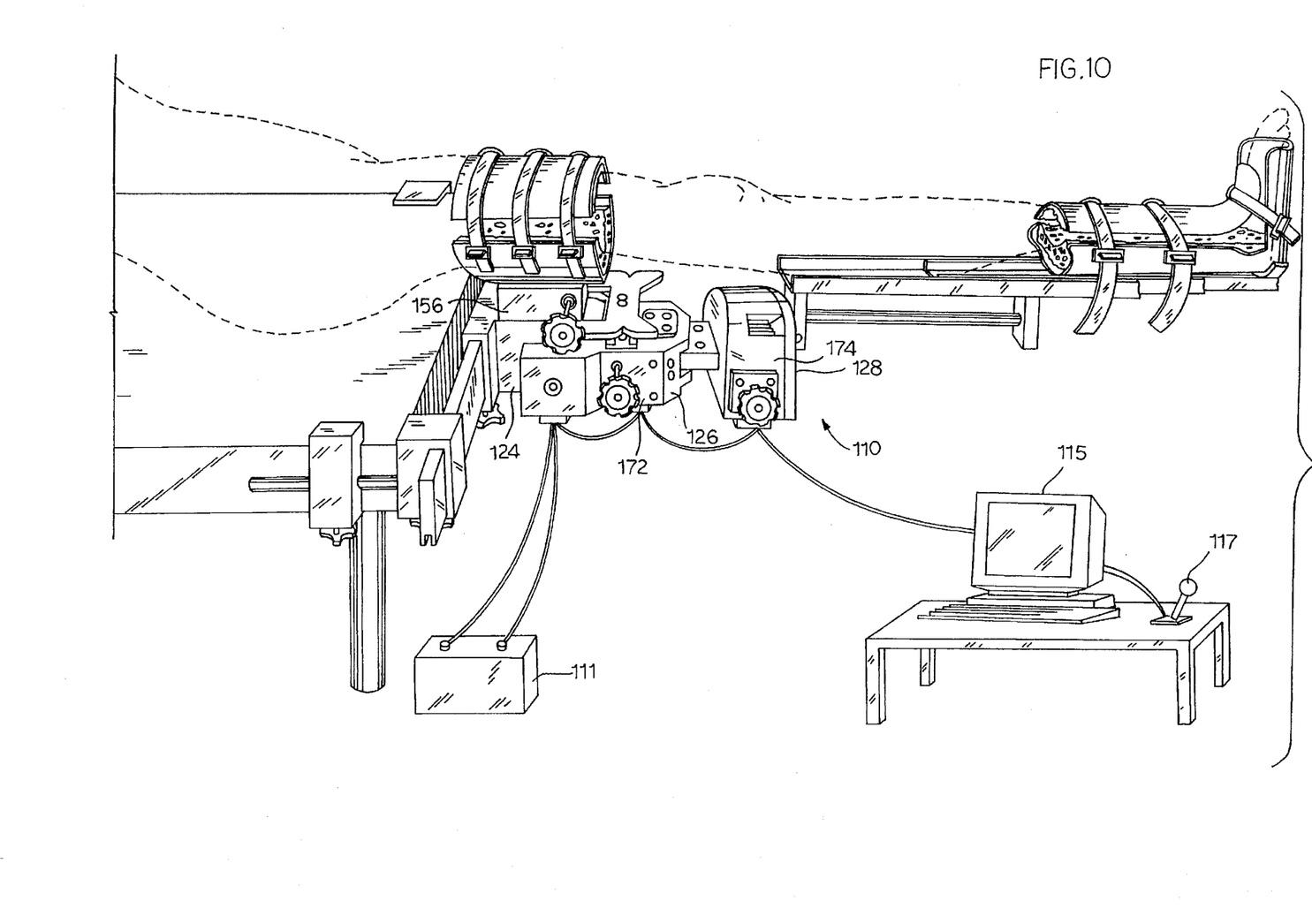
FIG. 10 is a perspective view of an alternative embodiment of the present invention orthopedic apparatus which utilizes a computer with a joystick controlling the adjustments of the various sections of the orthopedic apparatus.

Referring to FIG. 10, there is shown a perspective view of an alternative embodiment of the present invention orthopedic apparatus 110. This alternative embodiment is identical to the preferred embodiment as previously described in FIGS. 1 through 9 except that the gear mechanisms of the tilting, swinging and the extended rotatable sections 124, 126 and 128 are replaced with electrical motor driven means for adjusting the up-and-down tilting, lateral swinging, and axial rotation. The parts are numbered correspondingly with 100 added to each number. Only the modified components of the orthopedic apparatus 110 will be described.

The orthopedic apparatus 110 includes three motor driven means 156, 172 and 174 which are powered by a remote storage battery 111 or other electric power source. A computer 115 can be programed for precisely controlling the adjustments of the tilting section 124, the swinging section 126 and the extended rotatable section 128. A joy-stick 117 may also be provided for assisting the control and adjustments of the orthopedic apparatus 110.

The storage battery 111 is preferably one which will hold a substantial charge and which can be repeatedly charged. By way of example, an automobile lead-acid storage battery or any suitable battery can be used. The storage battery 111 can be mounted to a cabinet and powers the three motor driven means 156, 172 and 174 which control the tilting, swinging and extended rotatable sections 124, 126 and 128. The orthopedic apparatus 110 can also be powered by AC power.

It will be appreciated that the three motor driven means, the storage battery, the computer and joy-stick are all conventionally wired, and the description thereof will not be described since, it will not be too hard for one skilled in the art to electrically wire the orthopedic apparatus 110.

The present invention has many advantageous features including: (a) it eliminates the need for an assistant surgeon during orthopedic surgery; (b) it is very cost effective; (c) the various sections are independently controlled; and (d) it allows for three dimensional rotation.

Defined in detail, the present invention is an orthopedic apparatus for mechanically holding, maneuvering and maintaining a patient's leg during an orthopedic surgery and used in conjunction with an operating table which has two opposite clamps located adjacent to one end of the operating table, the apparatus comprising: (a) a clamping section, a tilting section, a swinging section, and an extended rotatable section; (b) said clamping section including an elongated cross bar with two opposite ends, two clamping blocks slidably attached at two opposite ends of the cross bar respectively, and a sliding block slidably attached on the cross bar between the two clamping blocks, where each clamping block has an integrally connected extension rod attachable to a respective one of said two opposite clamps on said operating table for holding the cross bar adjacent and parallel to said end of said operating table; (c) said tilting section including a tilting gear box integrally attached to said sliding block and having a self-locking tilting gear mechanism, a tilting part hingeably connected to the tilting gear box, a spring loaded lever mounted on the tilting part and engagable with the tilting gear mechanism for quick and rough adjustment of the tilting part, and a pair of tilting wheels connected to the tilting gear mechanism for fine adjustment of an up-and-down tilting of the tilting part; (d) said swinging section including a swinging gear box integrally attached to said tilting part of said tilting section and having a self-locking swinging gear mechanism, a swinging part hingeably connected to the swinging gear box, and a pair of swinging wheels connected to the swinging gear mechanism for adjusting a lateral swinging of the swinging part; (e) said extended rotatable section including a rotation gear box integrally attached to said swinging part of said swinging section and having a self-locking rotation gear mechanism, an elongated sliding track rotatably connected to the rotation gear box, and a pair of rotation wheels connected to the rotation gear mechanism for rotating the elongated sliding track about its longitudinal axis; (f) said elongated sliding track having a proximal portion and a distal portion, the proximal portion having two support shafts extending down and an elongated rod attached therebetween and having a proximal end connected to the rotation gear box, the distal portion having a foot holder for receiving and having means for securing thereto an ankle and foot of said patient and slidably attached to the proximal portion so that the length of the sliding track is adjustable to fit said patient's leg; and (g) a U-shaped thigh support holder attached to said tilting section for receiving a thigh of said patient and having means for securing the patient's thigh thereto; (h) whereby when said patient is lying on said operating table and a buttocks of said patient is located adjacent to said end of said operating table, a surgeon can slide said sliding block laterally to align said orthopedic apparatus with said patient's leg which is to be operated on, and independently adjust the tilting, swinging, length and rotation of said respective sections of said orthopedic apparatus to maneuver said patient's leg so that the leg is properly positioned and held in a proper position throughout the surgical operation, and the surgeon can further adjust the position of said patient's leg from time to time during the surgery with great accuracy.

Defined broadly, the present invention is an apparatus for mechanically holding, maneuvering and maintaining a patient's leg during an orthopedic surgery and used in conjunction with an operating table having at least one end, the apparatus comprising: (a) an attaching means section, a tilting section, a swinging section and a rotatable section; (b) said tilting section including a tilting gear box attached to said attaching means section and having a tilting gear mechanism, a tilting part hingeably connected to the tilting gear box, a lever mounted on the tilting part and engagable with the tilting gear mechanism for quick and rough adjustment of the tilting part, and a pair tilting wheels connected to the tilting gear mechanism for fine adjustment of an up-and-down tilting of the tilting part; (c) said swinging section including a swinging gear box attached to said tilting part of said tilting section and having a swinging gear mechanism, a swinging part hingeably connected to the swinging gear box, and a pair swinging wheels connected to the swinging gear mechanism for adjusting a lateral swinging of the swinging part; (d) said rotatable section including a rotation gear box attached to said swinging part of said swinging section and having a rotation gear mechanism, a sliding track rotatably connected to the rotation gear box, and a pair of rotation wheels connected to the rotation gear mechanism for rotating the sliding track about its longitudinal axis; and (f) said sliding track having a proximal portion and a distal portion, the proximal portion having two shafts extending down and a rod attached therebetween and having a proximal end connected to said rotation gear box, the distal portion having a foot holder for receiving and having means for securing thereto an ankle and foot of said patient and slidably attached to the proximal portion so that the length of the sliding track is adjustable to fit said patient's leg; (g) whereby when said patient is lying on said operating table and a buttocks of said patient is located adjacent to said at least one end of said operating table, a surgeon can align said apparatus with said patient's leg which is to be operated on, and independently adjust the tilting, swinging, length and rotation of said respective sections of said apparatus to maneuver said patient's leg so that the leg is properly positioned and held in a proper position throughout the surgical operation, and the surgeon can further adjust the position of said patient's leg from time to time during the surgery with great accuracy.

Defined even more broadly, the present invention is an apparatus for holding, maneuvering and maintaining a patient's leg during an orthopedic surgery and used in conjunction with an operating table, the apparatus comprising: (a) an attaching means attachable to said operating table, a tilting section, a swinging section and a rotatable section; (b) said tilting section including a tilting means attached to said attaching means, a tilting part hingeably connected to the tilting means and having means for adjusting an up-and-down tilting of the tilting part; (c) said swinging section including a swinging means attached to said tilting part of said tilting section, a swinging part hingeably connected to the swinging means and having means for adjusting a lateral swinging of the swinging part; and (d) said rotatable section including a rotation means attached to said swinging part of said swinging section, a sliding track rotatably connected to the rotation means and having means for rotating the sliding track about its longitudinal axis; (e) whereby when said patient is lying on said operating table, a surgeon can align said orthopedic apparatus with said patient's leg which is to be operated on, and independently adjust the tilting, swinging, length and rotation of said respective sections of said orthopedic apparatus to maneuver said patient's leg so that the leg is properly positioned and held in a proper position throughout the surgical operation, and the surgeon can further adjust the position of said patient's leg from time to time during the surgery with great accuracy.

Defined even more broadly, the present invention is an apparatus for holding, maneuvering and maintaining a patient's leg during an orthopedic surgery and used in conjunction with an operating table, the apparatus comprising: (a) an attaching means attachable to said operating table and a tilting section; and (b) said tilting section including a tilting means attached to said attaching means, a tilting part hingeably connected to the tilting means and having means for adjusting an up-and-down tilting of the tilting part; (c) whereby when said patient is lying on said operating table, a surgeon can align said apparatus with said patient's leg which is to be operated on, and independently adjust the tilting of said tilting section to maneuver said patient's leg so that the leg is properly positioned and held in a proper position throughout the surgical operation, and the surgeon can further adjust the position of said patient's leg from time to time during the surgery with great accuracy.

Also defined even more broadly, the present invention is an apparatus for holding, maneuvering and maintaining a patient's leg during an orthopedic surgery and used in conjunction with an operating table, the apparatus comprising: (a) an attaching means attachable to said operating table and a swinging section; and (b) said swinging section including a swinging means attached to said attaching means, a swinging part hingeably connected to the swinging means and having means for adjusting a lateral swinging of the swinging part; (c) whereby when said patient is lying on said operating table, a surgeon can align said apparatus with said patient's leg which is to be operated on, and independently adjust the swinging of said swinging section to maneuver said patient's leg so that the leg is properly positioned and held in a proper position throughout the surgical operation, and the surgeon can further adjust the position of said patient's leg from time to time during the surgery with great accuracy.

Further defined even more broadly, the present invention is an apparatus for holding, maneuvering and maintaining a patient's leg during an orthopedic surgery and used in conjunction with an operating table, the apparatus comprising: (a) an attaching means attachable to said operating table and a rotatable section; (b) said rotatable section including a rotation means attached to said attaching means, a sliding track rotatably connected to the rotation means and having means for rotating the sliding track about its longitudinal axis; and (c) said sliding track having a proximal portion and a distal portion, the proximal portion having two support shafts extending down and a rod attached therebetween and having a proximal end connected to the rotation means, the distal portion having a foot holder for receiving and having means for securing thereto an ankle and foot of said patient and slidably attached to the proximal portion so that the length of the sliding track is adjustable to fit said patient's leg; (d) whereby when said patient is lying on said operating table, a surgeon can align said apparatus with said patient's leg which is to be operated on, and independently adjust the length and rotation of said rotatable section to maneuver said patient's leg so that the leg is properly positioned and held in a proper position throughout the surgical operation, and the surgeon can further adjust the position of said patient's leg from time to time during the surgery with great accuracy Defined alternatively in detail, the present invention is an apparatus for holding, maneuvering and maintaining a patient's during an orthopedic surgery and used in conjunction with an operating table having at least one end, the apparatus comprising: (a) an attaching means section attachable to said at least one end of said operating table, a tilting section, a swinging section and a rotatable section; (b) said tilting section including a tilting motor driven means attached to said attaching means section, a tilting part hingeably connected to the tilting motor driven means and having means for adjusting an up-and-down tilting of the tilting part; (c) said swinging section including a swinging motor driven means attached to said tilting part of said tilting section, a swinging part hingeably connected to the swinging motor driven means and having means for adjusting a lateral swinging of the swinging part; (d) said rotatable section including a rotation motor driven means attached to said swinging part of said swinging section, a sliding track rotatably connected to the rotation motor driven means and having means for rotating the sliding track about its longitudinal axis; (e) said sliding track having a proximal portion and a distal portion, the proximal portion having two support shafts extending down and a rod attached therebetween and having a proximal end connected to said rotation motor driven means, the distal portion having a foot holder for receiving and having means for securing thereto an ankle and foot of said patient and slidably attached to the proximal portion so that the length of the sliding track is adjustable to fit said patient's leg; and (f) a U-shaped thigh support holder attached to said tilting section for receiving a thigh of said patient and having means for securing the patient's thigh thereto; (g) control means mounted on each one of said motor driven means for controlling the adjustments of said tilting part of said tilting section, said swinging part of said swinging section and said sliding track of said rotatable section; and (h) means for powering said apparatus and electrically connecting said tilting, swinging and rotation motor driven mechanism means through said control means respectively; (i) whereby when said patient is lying on said operating table and a buttocks of said patient is located adjacent to said at least one end of said operating table, a surgeon can align said apparatus with said patient's leg which is to be operated on, and independently adjust the tilting, swinging, length and rotation of said respective sections of said apparatus to maneuver said patient's leg so that the leg is properly positioned and held in a proper position throughout the surgical operation, and the surgeon can further adjust the position of said patient's leg from time to time during the surgery with great accuracy.

Defined also alternatively in detail, the present invention is an apparatus for holding, maneuvering and maintaining a patient's leg during an orthopedic surgery and used in conjunction with an operating table having at least one end, the apparatus comprising: (a) an attaching means attachable to said at least one end of said operating table, a tilting section, a swinging section and a rotatable section; (b) said tilting section including a tilting motor driven means attached to said attaching means, a tilting part hingeably connected to the tilting motor driven means and having means for adjusting an up-and-down tilting of the tilting part; (c) said swinging section including a swinging motor driven means attached to said tilting part of said tilting section, a swinging part hingeably connected to the swinging motor driven means and having means for adjusting a lateral swinging of the swinging part; (d) said rotatable section including a rotation motor driven means attached to said swinging part of said swinging section, a sliding track rotatably connected to the rotation motor driven means and having means for rotating the sliding track about its longitudinal axis; (e) said sliding track having a proximal portion and a distal portion, the proximal portion having two support shafts extending down and a rod attached therebetween and having a proximal end connected to said rotation motor driven means, the distal portion having a foot holder for receiving and having means for securing thereto an ankle and foot of said patient and slidably attached to the proximal portion so that the length of said sliding track is adjustable to fit said patient's leg; and (f) a U-shaped thigh support holder attached to said tilting section for receiving a thigh of said patient and having means for securing the patient's thigh thereto; (g) a computer mounted remote from said apparatus and having a joy-stick and a keyboard for automatically controlling the adjustments of said tilting part of said tilting section, said swinging part of said swinging section and said sliding track of said rotatable section; and (h) means for powering said apparatus and electrically connecting said tilting, swinging and rotation motor driven means through said computer respectively; (i) whereby when said patient is lying on said operating table and a buttocks of said patient is located adjacent to said at least one end of said operating table, a surgeon can align said apparatus with said patient's leg which is to be operated on, and independently adjust the tilting, swinging, length and rotation of said respective sections of said apparatus to maneuver said patient's leg so that the leg is properly positioned and held in a proper position throughout the surgical operation, and the surgeon can further adjust the position of said patient's leg from time to time during the surgery with great accuracy.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. An orthopedic apparatus for mechanically holding, maneuvering and maintaining a patient's leg during an orthopedic surgery and used in conjunction with an operating table which has two opposite clamps located adjacent to one end of the operating table, the apparatus comprising:

a. a clamping section, a tilting section, a swinging section, and an extended rotatable section;

b. said clamping section including an elongated cross bar with two opposite ends, two clamping blocks slidably attached at two opposite ends of the cross bar respectively, and a sliding block slidably attached on the cross bar between the two clamping blocks, where each clamping block has an integrally connected extension rod attachable to a respective one of said two opposite clamps on said operating table for holding the cross bar adjacent and parallel to said end of said operating table;

c. said tilting section including a tilting gear box integrally attached to said sliding block and having a self-locking tilting gear mechanism, a tilting part hingeably connected to the tilting gear box, a spring loaded lever mounted on the tilting part and engagable with the tilting gear mechanism for quick and rough adjustment of the tilting part, and a pair of tilting wheels connected to the tilting gear mechanism for fine adjustment of an up-and-down tilting of the tilting part;

d. said swinging section including a swinging gear box integrally attached to said tilting part of said tilting section and having a self-locking swinging gear mechanism, a swinging part hingeably connected to the swinging gear box, and a pair of swinging wheels connected to the swinging gear mechanism for adjusting a lateral swinging of the swinging part;

e. said extended rotatable section including a rotation gear box integrally attached to said swinging part of said swinging section and having a self-locking rotation gear mechanism, an elongated sliding track rotatably connected to the rotation gear box, and a pair of rotation wheels connected to the rotation gear mechanism for rotating the elongated sliding track about its longitudinal axis;

f. said elongated sliding track having a proximal portion and a distal portion, the proximal portion having two support shafts extending down and an elongated rod attached therebetween and having a proximal end connected to the rotation gear box, the distal portion having a foot holder for receiving and having means for securing thereto an ankle and foot of said patient and slidably attached to the proximal portion so that the length of the sliding track is adjustable to fit said patient's leg; and g. a U-shaped thigh support holder attached to said tilting section for receiving a thigh of said patient and having means for securing the patient's thigh thereto;

h. whereby when said patient is lying on said operating table and a buttocks of said patient is located adjacent to said end of said operating table, a surgeon can slide said sliding block laterally to align said orthopedic apparatus with said patient's leg which is to be operated on, and independently adjust the tilting, swinging, length and rotation of said respective sections of said orthopedic apparatus to maneuver said patient's leg so that the leg is properly positioned and held in a proper position throughout the surgical operation, and the surgeon can further adjust the position of said patient's leg from time to time during the surgery with great accuracy.

2. The orthopedic apparatus as defined in claim 1 further comprising disposable paddings attached to said foot holder of said elongated sliding track and said U-shaped thigh support holder.

3. The orthopedic apparatus as defined in claim 1 further comprising an upper inverted U-shaped thigh holder for applying pressure on top of the patient's thigh and having at least three loop eyelets through which the means for securing the patient's thigh are passed.

4. The orthopedic apparatus as defined in claim 1 further comprising an upper L-shaped cover for applying pressure on top of the patient's ankle and foot and having at least three loop eyelets through which the means for securing the patient's foot are passed.

5. The orthopedic apparatus as defined in claim 1 wherein said apparatus is made out of composite material.

6. The orthopedic apparatus as defined in claim 1 wherein said apparatus is made out of light-weight aluminum material.

7. An apparatus for mechanically holding, maneuvering and maintaining a patient's leg during an orthopedic surgery and used in conjunction with an operating table having at least one end, the apparatus comprising:

a. an attaching means section attachable to said at least one end of said operating table, a tilting section, a swinging section and a rotatable section;

b. said tilting section including a tilting gear box attached to said attaching means section and having a tilting gear mechanism, a tilting part hingeably connected to the tilting gear box, a lever mounted on the tilting part and engagable with the tilting gear mechanism for quick and rough adjustment of the tilting part, and a pair of tilting wheels connected to the tilting gear mechanism for fine adjustment of an up-and-down tilting of the tilting part;

c. said swinging section including a swinging gear box attached to said tilting part of said tilting section and having a swinging gear mechanism, a swinging part hingeably connected to the swinging gear box, and a pair of swinging wheels connected to the swinging gear mechanism for adjusting a lateral swinging of the swinging part;

d. said rotatable section including a rotation gear box attached to said swinging part of said swinging section and having a rotation gear mechanism, a sliding track rotatably connected to the rotation gear box, and a pair of rotation wheels connected to the rotation gear mechanism for rotating the sliding track about its longitudinal axis; and e. said sliding track having a proximal portion and a distal portion, the proximal portion having two shafts extending down and a rod attached therebetween and having a proximal end connected to the rotation gear box, the distal portion having a foot holder for receiving and having means for securing thereto an ankle and foot of said patient and slidably attached to the proximal portion so that the length of the sliding track is adjustable to fit said patient's leg;

f. whereby when said patient is lying on said operating table and a buttocks of said patient is located adjacent to said at least one end of said operating table, a surgeon can align said orthopedic apparatus with said patient's leg which is to be operated on, and independently adjust the tilting, swinging, length and rotation of said respective sections of said orthopedic apparatus to maneuver said patient's leg so that the leg is properly positioned and held in a proper position throughout the surgical operation, and the surgeon can further adjust the position of said patient's leg from time to time during the surgery with great accuracy.

8. The apparatus as defined in claim 7 further comprising a disposable padding attached to said foot holder of said sliding track.

9. The apparatus as defined in claim 7 further comprising a thigh support holder attached to said tilting section for receiving a thigh of said patient, and having means for securing the patient's thigh thereto.

10. The apparatus as defined in claim 9 wherein said thigh support holder has a disposable padding attached to said thigh support holder.

11. The apparatus as defined in claim 7 wherein said apparatus is made out of composite material.

12. The apparatus as defined in claim 7 wherein said end of the operating table includes at least two clamps, said attaching means section further includes a cross bar with two opposite ends, two clamping blocks slidably attached at two opposite ends of the cross bar respectively, and a sliding block slidably attached on the cross bar between the two clamping blocks, where each of the two clamping blocks has an integrally connected extension rod attachable to a respective one of said two clamps on the operating table.

13. An apparatus for mechanically holding, maneuvering and maintaining a patient's leg during an orthopedic surgery and used in conjunction with an operating table, the apparatus comprising:

a. an attaching means attachable to said operating table, a tilting section, a swinging section and a rotatable section;

b. said tilting section including a tilting means attached to said attaching means, a tilting part hingeably connected to the tilting means and having means for adjusting an up-and-down tilting of the tilting part;

c. said swinging section including a swinging means attached to said tilting part of said tilting section, a swinging part hingeably connected to the swinging means and having means for adjusting a lateral swinging of the swinging part; and d. said rotatable section including a rotation means attached to said swinging part of said swinging section, a sliding track rotatably connected to the rotation means and having means for rotating the sliding track about its longitudinal axis;

e. whereby when said patient is lying on said operating table, a surgeon can align said orthopedic apparatus with said patient's leg which is to be operated on, and independently adjust the tilting, swinging, length and rotation of said respective sections of said orthopedic apparatus to maneuver said patient's leg so that the leg is properly positioned and held in a proper position throughout the surgical operation, and the surgeon can further adjust the position of said patient's leg from time to time during the surgery with great accuracy.

14. The apparatus as defined in claim 13 wherein said sliding track has a proximal portion and a distal portion, the proximal portion having two shafts extending down and a rod attached therebetween and having a proximal end connected to the rotation means, the distal portion having a foot holder for receiving an ankle and foot of said patient and slidably attached to the proximal portion.

15. An apparatus for holding, maneuvering and maintaining a patient's leg during an orthopedic surgery and used in conjunction with an operating table which has at least two clamps at one end of the operating table, the apparatus comprising:

a. an attaching means attachable to said operating table and having a cross bar with two opposite ends, two clamping blocks slidably attached at the two opposite ends of the cross bar respectively, and a sliding block slidably attached on the cross bar between the two clamping blocks, where each of the two blocks has an integrally connected extension rod attachable to a respective one of said at least two clamps on said operating table; and b. a non-invasive tilting section having a tilting means attached to said attaching means, a non-invasive tilting part hingeably connected to the tilting means and having means for adjusting an up-and-down tilting of the tilting part and independently adjusting the tilting of said tilting section to maneuver said patient's leg so that said leg is properly positioned and held in a proper position throughout the surgical operation;

c. whereby when said patient is lying on said operating table, a surgeon can align said apparatus with said patient's leg which is to be operated on, and independently adjust the tilting of said tilting section to maneuver said patient's leg so that the leg is properly positioned and held in a proper position throughout the surgical operation, and the surgeon can further adjust the position of said patient's leg from time to time during the surgery with great accuracy.

16. The apparatus as defined in claim 15 further comprising a swinging section which includes a swinging means, a swinging part hingeably connected to the swinging means, and a pair of swinging wheels connected to the swinging means for adjusting a lateral swinging of the swinging part.

17. The apparatus as defined in claim 15 further comprising a rotatable section which includes a rotation means, a sliding track rotatably connected to the rotation means, and a pair of rotation wheels connected to the rotation means for rotating the sliding track about its longitudinal axis.

18. The apparatus as defined in claim 17 wherein said sliding track has a proximal portion and a distal portion, the proximal portion having two support shafts extending down and a rod attached therebetween and having a proximal end connected to said rotation means, the distal portion having a foot holder for receiving and having means for securing thereto an ankle and foot of said patient and slidably attached to the proximal portion so that the length of the sliding track is adjustable to fit said patient's leg.

19. An apparatus for holding, maneuvering and maintaining a patient's leg during an orthopedic surgery and used in conjunction with an operating table, the apparatus comprising:
  a. an attaching means attachable to said operating table;
  b. a swinging section having a swinging means attached to said attaching means, a swinging part hingeably connected to the swinging means and means for adjusting and maintaining a lateral swinging of the swinging part at any degree of tilting of said patient's leg; and
  c. tilting section having a tilting means, a tilting part hingeably connected to the tilting means and a pair of tilting wheels for adjusting an up and down tilting of the tilting part;
  d. whereby when said patient is lying on said operating table, a surgeon can align said apparatus with said patient's leg which is to be operated on, and independently adjust the swinging of said swinging section the tilting of said tilting section to maneuver said patient's leg so that the leg is properly positioned and held in a proper position throughout the surgical operation, and the surgeon can further adjust the position of said patient's leg from time to time during the surgery with great accuracy.

20. The apparatus as defined in claim 19 wherein the operating table includes at least two clamps at one end of the table and said attaching means includes a cross bar with two opposite ends, two clamping blocks slidably attached at two opposite ends of the cross bar respectively, and a sliding block slidably attached on the cross bar between the two clamping blocks, where each of the two clamping blocks has an integrally connected extension rod attachable to a respective one of said at least two clamps on the operating table.

21. The apparatus as defined in claim 19 further comprising a rotatable section which includes a rotation means, a sliding track rotatably connected to the rotation means, and a pair of rotation wheels connected to the rotation means for rotating the sliding track about its longitudinal axis.

22. The apparatus as defined in claim 21 wherein said sliding track has a proximal portion and a distal portion, the proximal portion having two support shafts extending down and a rod attached therebetween and having a proximal end connected to said rotation means, the distal portion having a foot holder for receiving and having means for securing thereto an ankle and foot of said patient and slidably attached to the proximal portion so that the length of the sliding track is adjustable to fit said patient's leg.

23. An apparatus for holding, maneuvering and maintaining a patient's leg during an orthopedic surgery and used in conjunction with an operating table, the apparatus comprising:
  a. an attaching means attachable to said operating table and a rotatable section;
  b. said rotatable section including a rotation means attached to said attaching means, a sliding track rotatably connected to the rotation means and having means for rotating the sliding track about its longitudinal axis; and
  c. said sliding track having a proximal portion and a distal portion, the proximal portion having two support shafts extending down and a rod attached therebetween and having a proximal end connected to the rotation means, the distal portion having a foot holder for receiving and having means for securing thereto an ankle and foot of said patient and slidably attached to the proximal portion so that the length of the sliding track is adjustable to fit said patient's leg;
  d. whereby when said patient is lying on said operating table, a surgeon can align said apparatus with said patient's leg which is to be operated on, and independently adjust the length and rotation of said rotatable section to maneuver said patient's leg so that the leg is properly positioned and held in a proper position throughout the surgical operation, and the surgeon can further adjust the position of said patient's leg from time to time during the surgery with great accuracy.

24. The apparatus as defined in claim 23 wherein said attaching means includes a cross bar with two opposite ends, two clamping blocks slidably attached at two opposite ends of the cross bar respectively, and a sliding block slidably attached on the cross bar between the two clamping blocks.

25. The apparatus as defined in claim 23 further comprising a tilting section which includes a tilting means, a tilting part hingeably connected to the tilting means, and a pair of tilting wheels for adjusting an up-and-down tilting of the tilting part.

26. The apparatus as defined in claim 23 further comprising a swinging section which includes a swinging means, a swinging part hingeably connected to the swinging means, and a pair of swinging wheels connected to the swinging means for adjusting a lateral swinging of the swinging part.

27. An apparatus for holding, maneuvering and maintaining a patient's during an orthopedic surgery and used in conjunction with an operating table having at least one end, the apparatus comprising:
  a. an attaching means section attachable to said at least one end of said operating table, a tilting section, a swinging section, and a rotatable section;
  b. said tilting section including a tilting motor driven means attached to said attaching means section, a tilting part hingeably connected to the tilting motor driven means and having means for adjusting an up-and-down tilting of the tilting part;
  c. said swinging section including a swinging motor driven means attached to said tilting part of said tilting section, a swinging part hingeably connected to the swinging motor driven means and having means for adjusting a lateral swinging of the swinging part;
  d. said rotatable section including a rotation motor driven means attached to said swinging part of said swinging section, a sliding track rotatably connected to the rotation motor driven means and having means for rotating the sliding track about its longitudinal axis;
  e. said sliding track having a proximal portion and a distal portion, the proximal portion having two support shafts extending down and a rod attached therebetween and having a proximal end connected to said rotation motor driven means, the distal portion having a foot holder for receiving and having means for securing thereto an ankle and foot of said patient and slidably attached to the proximal portion so that the length of the sliding track is adjustable to fit said patient's leg; and
  f. a U-shaped thigh support holder attached to said tilting section for receiving a thigh of said patient and having means for securing the patient's thigh thereto;
  g. control means mounted on each one of said motor driven means for controlling the adjustments of said tilting part of said tilting section, said swinging part of said swinging section and said sliding track of said rotatable section; and
  h. means for powering said apparatus and electrically connecting said tilting, swinging and rotation motor driven mechanism means through said control means respectively;

i. whereby when said patient is lying on said operating table and a buttocks of said patient is located adjacent to said at least one end of said operating table, a surgeon can align said apparatus with said patient's leg which is to be operated on, and independently adjust the tilting, swinging, length and rotation of said respective sections of said apparatus to maneuver said patient's leg so that the leg is properly positioned and held in a proper position throughout the surgical operation, and the surgeon can further adjust the position of said patient's leg from time to time during the surgery with great accuracy.

28. An apparatus for holding, maneuvering and maintaining a patient's leg during an orthopedic surgery and used in conjunction with an operating table having at least one end, the apparatus comprising:

a. an attaching means attachable to said at least one end of said operating table, a tilting section, a swinging section and a rotatable section;

b. said tilting section including a tilting motor driven means attached to said attaching means, a tilting part hingeably connected to the tilting motor driven means and having means for adjusting an up-and-down tilting of the tilting part;

c. said swinging section including a swinging motor driven means attached to said tilting part of said tilting section, a swinging part hingeably connected to the swinging motor driven means and having means for adjusting a lateral swinging of the swinging part;

d. said rotatable section including a rotation motor driven means attached to said swinging part of said swinging section, a sliding track rotatably connected to the rotation motor driven means and having means for rotating the sliding track about its longitudinal axis;

e. said sliding track having a proximal portion and a distal portion, the proximal portion having two support shafts extending down and a rod attached therebetween and having a proximal end connected to said rotation motor driven means, the distal portion having a foot holder for receiving and having means for securing thereto an ankle and foot of said patient and slidably attached to the proximal portion so that the length of said sliding track is adjustable to fit said patient's leg; and f. a U-shaped thigh support holder attached to said tilting section for receiving a thigh of said patient and having means for securing the patient's thigh thereto;

g. a computer mounted remote from said apparatus and having a joy-stick and a keyboard for automatically controlling the adjustments of said tilting part of said tilting section, said swinging part of said swinging section and said sliding track of said rotatable section; and h. means for powering said apparatus and electrically connecting said tilting, swinging and rotation motor driven means through said computer respectively;

i. whereby when said patient is lying on said operating table and a buttocks of said patient is located adjacent to said at least one end of said operating table, a surgeon can align said apparatus with said patient's leg which is to be operated on, and independently adjust the tilting, swinging, length and rotation of said respective sections of said apparatus to maneuver said patient's leg so that the leg is properly positioned and held in a proper position throughout the surgical operation, and the surgeon can further adjust the position of said patient's leg from time to time during the surgery with great accuracy.

* * * * *